US009498025B2

(12) United States Patent
Omarsson et al.

(10) Patent No.: US 9,498,025 B2
(45) Date of Patent: Nov. 22, 2016

(54) STRAP ATTACHMENT SYSTEM FOR ORTHOPEDIC DEVICE

(71) Applicant: OSSUR HF, Reykjavik (IS)

(72) Inventors: Bjorn Omarsson, Reykjavik (IS); Arni Thor Ingimundarson, Gardabaer (IS); Thorhalla Austman Hardardottir, Reykjavik (IS); Helgi Jonsson, Reykjavik (IS)

(73) Assignee: OSSUR HF, Reykjavik (IS)

( * ) Notice: Subject to any disclaimer, the term of this patent is extended or adjusted under 35 U.S.C. 154(b) by 187 days.

(21) Appl. No.: 14/247,699

(22) Filed: Apr. 8, 2014

(65) Prior Publication Data

US 2014/0298624 A1    Oct. 9, 2014

Related U.S. Application Data

(60) Provisional application No. 61/809,778, filed on Apr. 8, 2013.

(51) Int. Cl.
| *A44B 11/02* | (2006.01) |
| *A44B 13/00* | (2006.01) |
| *A44B 11/22* | (2006.01) |
| *A44B 11/25* | (2006.01) |
| *A61F 5/01* | (2006.01) |
| *A44B 11/00* | (2006.01) |

(52) U.S. Cl.
CPC .............. *A44B 11/02* (2013.01); *A44B 11/22* (2013.01); *A44B 11/2584* (2013.01); *A44B 11/2588* (2013.01); *A44B 13/0029* (2013.01); *A61F 5/01* (2013.01); *A61F 5/0123* (2013.01); *A44B 11/006* (2013.01); *Y10T 24/4745* (2015.01)

(58) Field of Classification Search
CPC .............. Y10T 24/45796; Y10T 24/45812; A44B 11/2588; A44B 11/2584; A44B 11/02; A44B 11/22; A44B 11/006; A44B 13/0029; A61F 5/0123
See application file for complete search history.

(56) References Cited

U.S. PATENT DOCUMENTS

| 667,768 A | 2/1901 | Poy |
| 777,585 A * | 12/1904 | Beatty ..................... A41F 1/006 24/68 B |
| 937,478 A | 10/1909 | Sims |
| 1,153,334 A | 9/1915 | Oswald |
| 1,227,700 A | 5/1917 | Tucker |
| 1,328,541 A | 1/1920 | Palmer |

(Continued)

FOREIGN PATENT DOCUMENTS

| DE | 846895 C | 8/1952 |
| DE | 100 04 561 A1 | 8/2001 |

(Continued)

OTHER PUBLICATIONS

Extended European Search Report from EP Application No. 10 17 2396, Oct. 8, 2010, 5 pages.

(Continued)

*Primary Examiner* — Robert J Sandy
(74) *Attorney, Agent, or Firm* — Workman Nydegger

(57) ABSTRACT

A strap attachment system includes a frame member having an opening, a strap, and a tab having a body and an attachment element defined by the body. The tab connects to the strap. A fastener element connects to the tab and is detachably and slidably mountable to the frame member by the opening.

11 Claims, 5 Drawing Sheets

(56) References Cited

U.S. PATENT DOCUMENTS

| | | | |
|---|---|---|---|
| 1,510,408 A | 9/1924 | Lychou | |
| 2,032,923 A | 3/1936 | Eldridge | |
| 2,467,907 A | 4/1949 | Peckham | |
| 2,573,866 A | 11/1951 | Murphy et al. | |
| 2,717,841 A | 9/1955 | Biefeld et al. | |
| 2,935,065 A | 5/1960 | Homier et al. | |
| 3,031,730 A | 5/1962 | Morin | |
| 3,046,981 A | 7/1962 | Biggs, Jr. et al. | |
| 3,089,486 A | 5/1963 | Pike | |
| 3,266,113 A | 8/1966 | Flanagan, Jr. | |
| 3,463,147 A | 8/1969 | Stubbs | |
| 3,514,313 A | 5/1970 | Martel et al. | |
| 3,520,765 A | 7/1970 | Bateman | |
| 3,528,412 A | 9/1970 | McDavid | |
| 3,561,436 A | 2/1971 | Gaylord, Jr. | |
| 3,581,741 A | 6/1971 | Rosman et al. | |
| 3,594,863 A | 7/1971 | Erb | |
| 3,594,865 A | 7/1971 | Erb | |
| 3,742,557 A | 7/1973 | Francois | |
| 3,752,619 A | 8/1973 | Menzin et al. | |
| 3,758,657 A | 9/1973 | Menzin et al. | |
| 3,789,842 A | 2/1974 | Froimson | |
| 3,851,357 A | 12/1974 | Ribich et al. | |
| 3,877,426 A | 4/1975 | Nirschl | |
| 3,916,077 A | 10/1975 | Damrau | |
| 3,927,881 A | 12/1975 | Lemelson et al. | |
| 3,945,046 A | 3/1976 | Stromgren | |
| 3,955,565 A | 5/1976 | Johnson, Jr. | |
| 4,193,395 A | 3/1980 | Gruber | |
| 4,204,532 A | 5/1980 | Lind et al. | |
| 4,240,414 A | 12/1980 | Theisler | |
| 4,269,179 A | 5/1981 | Burton et al. | |
| 4,269,181 A | 5/1981 | Delannoy | |
| 4,275,716 A | 6/1981 | Scott, Jr. | |
| 4,280,489 A | 7/1981 | Johnson, Jr. | |
| 4,291,072 A | 9/1981 | Barrett et al. | |
| 4,296,744 A | 10/1981 | Palumbo | |
| 4,304,560 A * | 12/1981 | Greenwood | F16G 1/24 24/580.11 |
| 4,336,279 A | 6/1982 | Metzger | |
| 4,372,298 A | 2/1983 | Lerman | |
| 4,381,768 A | 5/1983 | Erichsen et al. | |
| 4,386,723 A | 6/1983 | Mule | |
| 4,396,012 A | 8/1983 | Cobiski | |
| 4,470,857 A | 9/1984 | Casalou | |
| 4,472,461 A | 9/1984 | Johnson | |
| 4,506,661 A | 3/1985 | Foster | |
| 4,528,440 A | 7/1985 | Ishihara | |
| 4,554,913 A | 11/1985 | Womack et al. | |
| 4,572,170 A | 2/1986 | Cronk et al. | |
| 4,617,214 A | 10/1986 | Billarant | |
| 4,632,098 A | 12/1986 | Grundei et al. | |
| 4,677,713 A * | 7/1987 | Copp | A44B 11/2588 24/573.11 |
| 4,693,921 A | 9/1987 | Billarant et al. | |
| D292,529 S | 10/1987 | Saare | |
| 4,768,500 A | 9/1988 | Mason et al. | |
| 4,775,310 A | 10/1988 | Fischer | |
| D298,568 S | 11/1988 | Womack et al. | |
| 4,782,605 A | 11/1988 | Chapnick | |
| 4,791,916 A | 12/1988 | Paez | |
| 4,794,028 A | 12/1988 | Fischer | |
| 4,801,138 A | 1/1989 | Airy et al. | |
| 4,802,939 A | 2/1989 | Billarant et al. | |
| 4,805,606 A | 2/1989 | McDavid, III | |
| 4,854,308 A | 8/1989 | Drillo | |
| 4,856,501 A | 8/1989 | Castillo et al. | |
| 4,856,502 A | 8/1989 | Ersfeld et al. | |
| 4,872,243 A | 10/1989 | Fischer | |
| 4,922,929 A | 5/1990 | DeJournett | |
| 4,933,035 A | 6/1990 | Billarant et al. | |
| 4,953,543 A | 9/1990 | Grim et al. | |
| 4,961,544 A | 10/1990 | Bidoia | |
| 4,966,133 A | 10/1990 | Kausek | |
| 4,989,593 A | 2/1991 | Campagna et al. | |
| 4,991,574 A | 2/1991 | Pocknell | |
| 4,991,640 A | 2/1991 | Verkindt et al. | |
| 5,016,621 A | 5/1991 | Bender | |
| 5,018,514 A | 5/1991 | Grood et al. | |
| 5,020,196 A | 6/1991 | Panach et al. | |
| 5,022,109 A | 6/1991 | Pekar | |
| 5,063,916 A | 11/1991 | France et al. | |
| 5,067,772 A | 11/1991 | Koa | |
| 5,077,870 A | 1/1992 | Melbye et al. | |
| 5,085,210 A | 2/1992 | Smith, III | |
| 5,112,296 A | 5/1992 | Beard et al. | |
| 5,154,682 A | 10/1992 | Kellerman | |
| 5,157,813 A | 10/1992 | Carroll | |
| 5,181,331 A | 1/1993 | Berger | |
| 5,242,379 A | 9/1993 | Harris et al. | |
| 5,267,951 A | 12/1993 | Ishii | |
| 5,277,697 A | 1/1994 | France et al. | |
| 5,277,698 A | 1/1994 | Taylor | |
| 5,288,287 A | 2/1994 | Castillo et al. | |
| 5,302,169 A | 4/1994 | Taylor | |
| 5,314,455 A | 5/1994 | Johnson, Jr. et al. | |
| 5,316,547 A | 5/1994 | Gildersleeve | |
| 5,322,729 A | 6/1994 | Heeter et al. | |
| 5,334,135 A | 8/1994 | Grim et al. | |
| 5,344,135 A | 9/1994 | Isobe et al. | |
| 5,368,549 A | 11/1994 | McVicker | |
| 5,383,845 A | 1/1995 | Nebolon | |
| 5,397,296 A | 3/1995 | Sydor et al. | |
| 5,415,625 A | 5/1995 | Cassford et al. | |
| 5,431,623 A | 7/1995 | Rice | |
| 5,437,619 A | 8/1995 | Malewicz et al. | |
| 5,445,602 A | 8/1995 | Grim et al. | |
| 5,449,341 A | 9/1995 | Harris | |
| 5,458,565 A | 10/1995 | Tillinghast, III et al. | |
| 5,468,219 A | 11/1995 | Crippen | |
| 5,472,413 A | 12/1995 | Detty | |
| 5,474,524 A | 12/1995 | Carey | |
| 5,497,513 A | 3/1996 | Arabeyre et al. | |
| 5,500,268 A | 3/1996 | Billarant | |
| 5,512,039 A | 4/1996 | White | |
| 5,513,658 A | 5/1996 | Goseki | |
| 5,514,081 A | 5/1996 | Mann | |
| 5,527,269 A | 6/1996 | Reithofer | |
| 5,540,982 A | 7/1996 | Scholz et al. | |
| 5,542,911 A | 8/1996 | Cassford et al. | |
| 5,562,605 A | 10/1996 | Taylor | |
| 5,599,288 A | 2/1997 | Shirley et al. | |
| 5,614,045 A | 3/1997 | Billarant | |
| 5,635,201 A | 6/1997 | Fabo | |
| 5,638,588 A | 6/1997 | Jungkind | |
| 5,654,070 A | 8/1997 | Billarant | |
| 5,656,226 A | 8/1997 | McVicker | |
| 5,665,449 A | 9/1997 | Billarant | |
| 5,695,452 A | 12/1997 | Grim et al. | |
| 5,713,837 A | 2/1998 | Grim et al. | |
| D392,877 S | 3/1998 | Eguchi | |
| 5,737,854 A | 4/1998 | Sussmann | |
| 5,759,167 A | 6/1998 | Shields, Jr. et al. | |
| 5,769,808 A | 6/1998 | Matthijs et al. | |
| 5,774,902 A | 7/1998 | Gehse | |
| 5,795,640 A | 8/1998 | Billarant | |
| 5,823,981 A | 10/1998 | Grim et al. | |
| 5,840,398 A | 11/1998 | Billarant | |
| 5,857,988 A | 1/1999 | Shirley | |
| 5,857,989 A | 1/1999 | Smith, III | |
| 5,865,776 A | 2/1999 | Springs | |
| 5,865,777 A | 2/1999 | Detty | |
| 5,865,782 A | 2/1999 | Fareed | |
| 5,873,848 A | 2/1999 | Fulkerson | |
| 5,891,061 A | 4/1999 | Kaiser | |
| 5,900,303 A | 5/1999 | Billarant | |
| 5,916,187 A | 6/1999 | Brill | |
| 5,948,707 A | 9/1999 | Crawley et al. | |
| 5,971,946 A | 10/1999 | Quinn | |
| 6,010,474 A | 1/2000 | Wycoki | |
| 6,021,780 A | 2/2000 | Darby | |
| 6,022,617 A | 2/2000 | Calkins | |
| 6,024,712 A | 2/2000 | Iglesias et al. | |
| 6,063,048 A | 5/2000 | Bodenschatz et al. | |

(56) References Cited

U.S. PATENT DOCUMENTS

| | | |
|---|---|---|
| 6,110,138 A | 8/2000 | Shirley |
| 6,111,138 A | 8/2000 | Van Wijck et al. |
| 6,142,965 A | 11/2000 | Mathewson |
| 6,152,893 A | 11/2000 | Pigg et al. |
| 6,159,583 A | 12/2000 | Calkins |
| 6,250,651 B1 | 6/2001 | Reuss et al. |
| 6,254,554 B1 | 7/2001 | Turtzo |
| 6,267,741 B1 | 7/2001 | Lerman |
| RE37,338 E | 8/2001 | McVicker |
| 6,287,268 B1 | 9/2001 | Gilmour |
| 6,289,558 B1 | 9/2001 | Hammerslag |
| 6,360,404 B1 | 3/2002 | Mudge et al. |
| 6,368,295 B1 | 4/2002 | Lerman |
| 6,402,713 B1 | 6/2002 | Doyle |
| 6,405,731 B1 | 6/2002 | Chiang |
| 6,413,232 B1 | 7/2002 | Townsend et al. |
| 6,416,074 B1 | 7/2002 | Maravetz et al. |
| 6,461,318 B2 | 10/2002 | Freeman et al. |
| 6,485,776 B2 | 11/2002 | Janusson et al. |
| 6,520,926 B2 | 2/2003 | Hall |
| 6,540,703 B1 | 4/2003 | Lerman |
| 6,540,709 B1 | 4/2003 | Smits |
| 6,543,158 B2 | 4/2003 | Dieckhaus |
| D477,409 S | 7/2003 | Mills et al. |
| 6,592,538 B1 | 7/2003 | Hotchkiss et al. |
| 6,592,539 B1 | 7/2003 | Einarsson et al. |
| 6,596,371 B1 | 7/2003 | Billarant et al. |
| 6,598,250 B1 | 7/2003 | Pekar |
| 6,656,142 B1 | 12/2003 | Lee |
| 6,666,894 B2 | 12/2003 | Perkins et al. |
| 6,689,080 B2 | 2/2004 | Castillo |
| 6,726,641 B2 | 4/2004 | Chiang et al. |
| 6,735,819 B2 | 5/2004 | Iverson et al. |
| 6,769,155 B2 | 8/2004 | Hess et al. |
| 6,773,411 B1 | 8/2004 | Alvarez |
| 6,861,379 B1 | 3/2005 | Blaszcykiewicz |
| 6,861,371 B2 | 5/2005 | Blaszcykiewicz |
| 6,898,804 B2 | 5/2005 | Sandler |
| 6,898,826 B2 | 5/2005 | Draper et al. |
| 6,936,020 B2 | 8/2005 | Davis |
| D519,637 S | 4/2006 | Nordt, III et al. |
| D519,638 S | 4/2006 | Nordt, III et al. |
| 7,025,738 B2 | 4/2006 | Hall |
| D520,141 S | 5/2006 | Nordt, III et al. |
| D521,644 S | 5/2006 | Nordt, III et al. |
| 7,037,287 B2 | 5/2006 | Cormier et al. |
| 7,150,721 B2 | 12/2006 | Houser |
| 7,161,056 B2 | 1/2007 | Gudnason et al. |
| 7,169,720 B2 | 1/2007 | Etchells et al. |
| 7,198,610 B2 | 4/2007 | Ingimundarson et al. |
| 7,303,539 B2 | 12/2007 | Binder et al. |
| 7,367,958 B2 | 5/2008 | McBean et al. |
| 7,448,115 B2 | 11/2008 | Howell et al. |
| 7,762,973 B2 | 7/2010 | Einarsson et al. |
| 7,874,996 B2 | 1/2011 | Weinstein et al. |
| 7,937,973 B2 | 5/2011 | Sorensen et al. |
| 2001/0020143 A1 | 9/2001 | Stark et al. |
| 2001/0056251 A1 | 12/2001 | Peters |
| 2002/0032397 A1 | 3/2002 | Coligado |
| 2002/0077574 A1 | 6/2002 | Gildersleeve et al. |
| 2002/0082542 A1 | 6/2002 | Hall |
| 2002/0095750 A1 | 7/2002 | Hammerslag |
| 2002/0132086 A1 | 9/2002 | Su-Tuan |
| 2003/0032907 A1 | 2/2003 | Prahl |
| 2003/0069531 A1 | 4/2003 | Hall |
| 2003/0204156 A1 | 10/2003 | Nelson et al. |
| 2004/0002674 A1 | 1/2004 | Sterling |
| 2004/0054311 A1 | 3/2004 | Sterling |
| 2004/0058102 A1 | 3/2004 | Baychar |
| 2004/0137178 A1 | 7/2004 | Janusson et al. |
| 2004/0137192 A1 | 7/2004 | McVicker |
| 2004/0153016 A1 | 8/2004 | Salmon et al. |
| 2004/0176715 A1 | 9/2004 | Nelson |
| 2004/0199095 A1 | 10/2004 | Frangi |
| 2004/0225245 A1 | 11/2004 | Nelson |
| 2004/0267179 A1 | 12/2004 | Lerman |
| 2005/0020951 A1 | 1/2005 | Gaylord et al. |
| 2005/0038367 A1 | 2/2005 | McCormick et al. |
| 2005/0081339 A1 | 4/2005 | Sakabayashi |
| 2005/0159691 A1 | 7/2005 | Turrini et al. |
| 2005/0160627 A1 | 7/2005 | Dalgaard et al. |
| 2006/0015980 A1 | 1/2006 | Nordt, III et al. |
| 2006/0020237 A1 | 1/2006 | Nordt, III et al. |
| 2006/0026732 A1 | 2/2006 | Nordt, III et al. |
| 2006/0026733 A1 | 2/2006 | Nordt, III et al. |
| 2006/0026736 A1 | 2/2006 | Nordt, III et al. |
| 2006/0030802 A1 | 2/2006 | Nordt, III et al. |
| 2006/0030803 A1 | 2/2006 | Nordt, III et al. |
| 2006/0030804 A1 | 2/2006 | Nordt, III et al. |
| 2006/0030805 A1 | 2/2006 | Nordt, III et al. |
| 2006/0030806 A1 | 2/2006 | Nordt, III et al. |
| 2006/0070164 A1 | 4/2006 | Nordt, III et al. |
| 2006/0070165 A1 | 4/2006 | Nordt, III et al. |
| 2006/0084899 A1 | 4/2006 | Verade et al. |
| 2006/0090806 A1 | 5/2006 | Friedline et al. |
| 2006/0116619 A1 | 6/2006 | Weinstein et al. |
| 2006/0135902 A1 | 6/2006 | Ingimundarson et al. |
| 2006/0135903 A1 | 6/2006 | Ingimundarson et al. |
| 2006/0155229 A1 | 7/2006 | Ceriani et al. |
| 2006/0191110 A1 | 8/2006 | Howell et al. |
| 2007/0083136 A1 | 4/2007 | Einarsson |
| 2007/0167892 A1 | 7/2007 | Gramza et al. |
| 2007/0185425 A1 | 8/2007 | Einarsson et al. |
| 2007/0225824 A1 | 9/2007 | Einarsson |
| 2008/0034459 A1 | 2/2008 | Nordt, III et al. |
| 2008/0229556 A1 | 9/2008 | Hammer |
| 2009/0099562 A1 | 4/2009 | Ingimundarson et al. |
| 2009/0126413 A1 | 5/2009 | Sorensen et al. |
| 2010/0068464 A1 | 3/2010 | Meyer |
| 2010/0125231 A1 | 5/2010 | Knecht |
| 2011/0057466 A1 | 3/2011 | Sachee et al. |
| 2011/0275970 A1 | 11/2011 | Paulos et al. |
| 2012/0010547 A1 | 1/2012 | Hinds |
| 2012/0046585 A1 | 2/2012 | Lee et al. |
| 2012/0090624 A1 | 4/2012 | Chang |
| 2012/0109031 A1 | 5/2012 | Vollbrecht et al. |
| 2014/0121579 A1 | 5/2014 | Hinds |

FOREIGN PATENT DOCUMENTS

| | | |
|---|---|---|
| DE | 20 2004 012892 U1 | 11/2004 |
| EP | 0050769 A1 | 5/1982 |
| EP | 0 196 204 A2 | 10/1986 |
| EP | 0611069 B1 | 8/1994 |
| EP | 2612626 A2 | 7/2013 |
| FR | 2399811 A1 | 3/1979 |
| FR | 2553996 A1 | 5/1985 |
| FR | 2766359 A1 | 1/1999 |
| GB | 1209413 A | 10/1970 |
| GB | 2136294 A | 9/1984 |
| GB | 2 455 972 A | 7/2009 |
| WO | 88/01855 A1 | 3/1988 |
| WO | 94/00082 A1 | 1/1994 |
| WO | 00/49982 A1 | 8/2000 |
| WO | 00/70984 A1 | 11/2000 |
| WO | 2006/015599 A1 | 2/2006 |
| WO | 2006/069221 A2 | 6/2006 |
| WO | 2006/069222 A2 | 6/2006 |
| WO | 2008/115376 A1 | 9/2008 |
| WO | 2010/117749 A2 | 10/2010 |
| WO | 2011/073803 A2 | 6/2011 |

OTHER PUBLICATIONS

Extended European Search Report from EP Application No. 08 74 2047, Jun. 6, 2013, 6 pages.

International Search Report and Written Opinion from International PCT Application No. PCT/US2014/014192, May 20, 2014.

International Search Report and Written Opinion from PCT Application No. PCT/IB2010/003540, Oct. 13, 2011.

International Search Report and Written Opinion from PCT Application No. PCT/US2008/03237, Jul. 14, 2008.

(56) References Cited

OTHER PUBLICATIONS

Advertisement: "Custom Engineered Fabrics and Products for Advanced High Performance," 1 page, Gehring Textiles retrieved from the Internet on Dec. 15, 2000; http://www.gehringtextiles.com/d3.html.
Article: "Thermoplastic Elastomers TPE, TPR, TPV," 6 pages, retrieved from the Internet on Mar. 14, 2007; http://www.bpf.com.uk/bpfindustry/plastics_materials_thermplasrubber_TBR.cfm.
Advertisement: "Axiom." 3 pages, Bledsoe by Medical Technology, Inc., retrieved from the Internet Jun. 15, 2005; http://www.bledsoebrace.com/custom/axiom.asp.
Advertisement: "Bellacure: The Treatment Device," 6 pages, Bellacure, Inc., retrieved from the Internet on Jan. 5, 2006, http://www.bellacure.com/products/index.htm.
Advertisement: "Lerman 3-Point Knee Orthosis," 2 pages, Becker Orthopedic of Troy, MI, retrieved from the Internet on Feb. 23, 2006, http://www.beckerortho.com/knee/3-point.html.
Advertisement: "M2 Inc. Parts Catalog," 3 pages, M2 Inc of Winooski, VT, retrieved from the Internet on Mar. 29, 2005, http:www.m2intl.com/medical.MedCisr.htm.
Advertisement: "McDavid Knee Guard and 155 Ligament Augmentation System," 3 pages, Advanced Brace of Irving, TX, retrieved from the Internet on Mar. 8, 2005, http://www.supports4u.com/mcdavid/kneeguard.htm.
Advertisement: "Triax," 1 page, LANXESS AG, retrieved from the Internet on Mar. 8, 2005, http://www.techcenter.lanxess.com/sty/emea/en/products/description/57/index.jsp?print=true&pid=57.
Advertising brochure: "Anderson Knee Stabler," 4 pages, Omni Scientific, Inc. of Lafayette, CA, (2005).
Advertising brochure: "Fusion," 6 pages, Breg, Inc. of Vista, CA (2005).
Advertising brochure: "Fustion XT," 2 pages, Breg, Inc. of Vista, CA (2005.).
Advertising brochure: GII Unloader Select, 2 pages, Ossur hf of Reykjavik, Iceland, retrieved from the Internet on Mar. 8, 2005, http:www.ossur.com/print.asp?PageID-1729.
Advertising brochure: "Lerman Multi-Ligamentus Knee Control Orthosis," 2 pages, Zinco Industries, Inc. of Montrose, CA (1985).
Advertising brochure: "NuKO Camp," 6 pages, Camp International, Inc., Jackson, MI (1984).
Advertising brochure: "OTI Brace," 4 pages, Orthopedic Technology, Inc., of San Leandro, CA (2005).
Advertising brochure: "The Four Axioms of Functional Bracing," 1 page, Bledsoe by Medical Technology, Inc. (2005).
Advertising brochure: "The Leader in Knee Motion Management," 8 pages, Donjoy, Carlsbad, CA (2005).
Advertising brochure: "The Lenox Hill Lightweight," 1 page, Lenox Hill Brace, Inc., New York, NY (2005).
Advertising brochure: "XCL System", 2 pages, Innovation Sports of Foothill Ranch, CA (2005).
Cousins, S., et al., "An Orthosis for Medial or Lateral Stabilization of Arthritic Knees", Orthotics and Prosthetics, vol. 29, No. 4, pp. 21-26, Dec. 1975.
"Osteoarthritis of the Knee: an information booklet," 12 pages, Arthritis Research Campaign, retrieved from the Internet on Dec. 14, 2004, http://www.arc.org.uk/about_arth/booklets/6027/6027.htm.
Reference: "Anatomical Planes," 1 page, retrieved from the Internet on Mar. 26, 2005, http://www.spineuniverse.com/displayarticle/phpo/article1023.html.
Technical Manual: "Bellacure: Restore Your Lifestyle," 10 pages, Bellacure, Inc. (2005).
Technical Manual: "BOA Technology", 3 pages, BOA Technology, Inc. of Steamboat Springs, CO (2005).
"Information on Flexible Polyurethane Foam", In Touch, vol. 4, No. 3, Jul. 1994, 5 pages.
Advertising brochure: "Freedom to Perform—Fusion", 5 pages, (2005).
Advertising brochure: "The 9 Innovations of the Axiom Custom Brace", 1 page, Bledsoe, Medical Technology, Inc. (2005).
International Search Report and Written Opinion of the International Searching Authority from International Application No. PCT/US2014/010410, mailed May 2, 2014.
International Search Report and Written Opinion from International Application No. PCT/US2013/069558, Jul. 3, 2014.
International Search Report and Written Opinion from International Application No. PCT/US2014/010407, Jul. 10, 2014.
International Search Report and Written Opinion from International Application No. PCT/US2014/033266, Jul. 23, 2014.
International Search Report from PCT Application No. PCT/US2016/012346, May 6, 2016.

\* cited by examiner

STRAP ATTACHMENT SYSTEM FOR ORTHOPEDIC DEVICE

FIELD OF ART

The embodiments of this disclosure are directed to strap attachment systems for an orthopedic device or other devices requiring a strap.

BACKGROUND

Braces and supports, such as knee braces, have a tendency to migrate on the limbs of the user during use. There are various reasons for this migration, including, but not limited to, improper fitting and poor anchoring of the brace to the user. Two common methods are used to counter this migration, namely strapping and using high friction interfaces.

Skin irritation may arise due to mechanical irritation between the frictional interface and the skin due to excessive rubbing. Skin irritation may be caused by excessive shear forces applied from a high friction interface material that moves on skin due to non-anatomical movement of the brace relative to the user's limb. Elimination of the frictional material or the creation of a barrier between the skin and frictional material will reduce skin irritation.

For those users that experience skin irritation, a softer liner or sleeve with less friction against the skin, for example, doeskin, textile, foam, etc., can replace or be used in combination with a high friction interface. With the reduction of friction, however, there is a tendency that the liner leads to increased migration. For these users, therefore, strapping may be the only option to avoid migration.

Conventional methods for attaching straps to braces rarely permit pivoting of the strap. Instead, the strap is fixed in location and may resist movement of the user's limb and create discomfort. Failing to pivot according to the user's movement also creates problems with conformation to user anatomy and fit.

Pressure points may arise due to the bunching of straps over certain regions of a user's anatomy, for example, over the user's popliteal, and of exposed portions of hard shell or frame members of the brace. Often braces lack the flexibility to allow a clinician or user to reposition the anchor of a strap over the hard shell or frame member to avoid pressure points. Also, as when repositioning the strap, the clinician or user needs the ability to position the strap anchor to avoid migration.

SUMMARY

Various strap attachment system embodiments described in this disclosure are provided for eliminating or reducing frictional interfaces that may lead to skin irritation. The embodiments are arranged for preventing bunching and eliminating pressure points due to exposed portions of the frame of a brace or support. The embodiments permit pivoting and adjustment relative to the anatomy of the user. The embodiments are adjustable in locations on the frame of the brace or support, allowing flexibility for the clinician or user to position strap attachment system in locations that will assist in prevention of migration and pressure points.

In addressing migration, the strap attachment systems supplant or complement friction interfaces. The strap attachment systems preferably eliminate a need for tools, and serve as an anchor point with or without a friction interface. The strap attachment systems may also be used in combination with various pads having little or no friction interface.

An embodiment of the strap attachment system includes a frame member having an opening, a strap, a tab having a body and a fastener element. The fastener element is detachably and slidably mountable to the frame member via the opening. The tab may define an attachment element with which the fastener element removably engages to secure the tab to the frame member. The tab may rotatably connect to the fastener element.

The fastener element preferably defines upper and lower portions. The lower portion is arranged to abut a first surface of the frame member, and the upper portion is arranged to extend over a second surface of the frame member by a clearance. The tab may secure between the upper portion and the second surface of the frame member within the clearance.

The shaft of the fastener element preferably has portions defining a dimension resisting turning within the opening of frame member such that upon overcoming resistance within the opening, the shaft has a dimension generally the same as a width of the opening so as to permit sliding of the fastener element within the opening without rotation. According to a variation, the shaft defines a generally square cross-section having rounded corners. The rounded corners generally provide for resistance to twisting against a periphery of the frame member defining the at least one opening.

Another embodiment of a strap attachment system includes a frame member having an opening, a strap and a tab having a body and a fastener element extending from the body and arranged to be engaged to the frame member via the opening. The tab is slidably movable relative to the frame member within the opening.

The fastener element includes a shaft carrying a crosshead, the shaft having a height at the least the same as a thickness of the frame member. The cross-head may define a first width substantially the same as a second width defined by the opening. The cross-head may have a first length greater than the second width defined by the opening. The first width of the cross-head may be less than the second length defined by the opening, where the difference in length between the first width and the second length define a length of travel of the tab relative to the frame member within the opening.

The shaft may define first and second side walls opposed from one another and spaced apart by a third width. The third width may be substantially the same as the second width of the opening. The first and second side walls may be arranged perpendicular to a first length of the cross-head. The shaft may define first and second end portions opposed from one another and be arranged generally perpendicular to the side first and second side walls.

A distance between the first and second end portions may be greater than a second width defined by the opening. The shaft may be insertable through the opening wherein the first and second side walls are arranged perpendicular to the second width. The at least one frame member may be resilient as the shaft is pressed through the opening, and the shaft is arranged for rotation within the opening so as to arrange the first and second side walls parallel to the second width.

The dimensional relationships of the shaft and cross-pin, and the opening may be interchangeably used for any of the embodiments described herein.

The tab body may be substantially flat and the shaft may extend perpendicularly from a first end of the body. The body may define a second end flaring outwardly from the first end of the body, and the cross-head extends generally parallel to the second end of the body.

The body of the tab may taper toward a first end tip where the fastener element may be located, and the body may flare outwardly toward a second end where the strap attaches to the tab. The tab may define a plurality of opening that secure to securing elements connecting the tab to the strap.

A method includes attaching a strap connected to a tab to a frame member having an opening using certain embodiments described herein. The method includes arranging a fastener element having a shaft carrying a cross-head in the opening by orienting a width of the cross-head parallel to a length of the opening. The cross-head may be inserted through the opening so as extend over a surface of the frame member. The fastener element may be turned so the width of the cross-head is perpendicular to the opening with the shaft extending through the opening. The fastener element connects the strap to the frame member.

BRIEF DESCRIPTION OF THE DRAWINGS

These and other features, aspects, and advantages of the present invention will become better understood regarding the following description, appended claims, and accompanying drawings.

Figure 1:
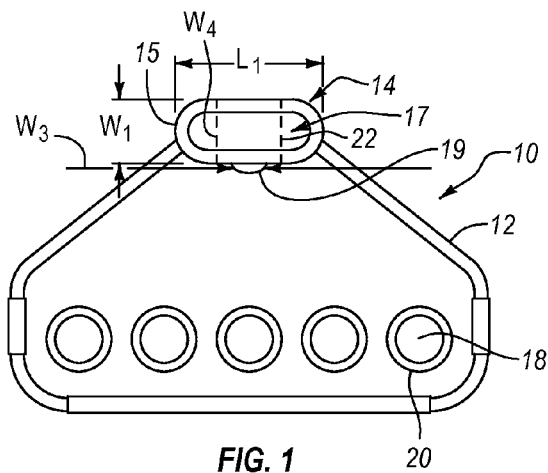
FIG. 1 is a top plan view of an embodiment of a tab of an embodiment of a strap attachment system.
Figure 2:
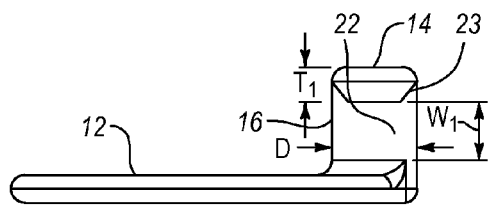
FIG. 2 is an elevational view of the tab of FIG. 1.

In the various figures, similar elements are provided with similar reference numbers. The drawing figures are not drawn to scale, or proportion, but instead are drawn to provide a better understanding of the components, and are not intended to be limiting in scope, but rather provide exemplary illustrations.

DETAILED DESCRIPTION OF VARIOUS EMBODIMENTS

Referring to the strap attachment system embodiment of FIGS. 1-4, a tab 10 has a tab body 12 and a fastener element including a shaft 16 and a cross-head 14 extending from the shaft 16. The tab body 12 has a generally flat configuration and includes a plurality of apertures 18 having a recessed border 20. The apertures are adapted for receiving and securing securing elements 90, such as cables, threads, or other means, for securing the tab body 12 to a strap 80. The tab body 12 defines a generally triangular configuration having a greatest width at a tail end corresponding to the apertures 18, and tapering toward a tip 24 carrying the cross-head 14.

The cross-head 14 defines first and second flanges 15, 17 extending beyond the shaft 16. The shaft has flat side walls 22 that extend generally perpendicular to the flanges 15, 17. The flat side walls 22 permit insertion into openings formed on frame members. The side walls 22 are not limited to being flat, but may have a curved profile, slanted profile or other suitable shape.

Figure 3:
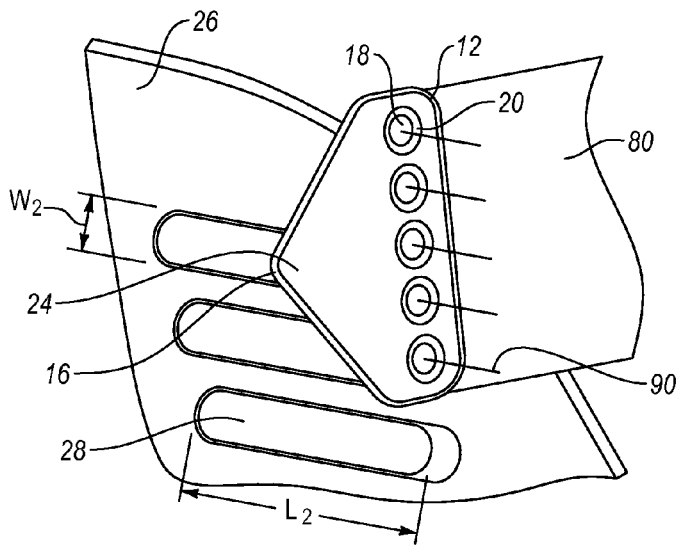
FIG. 3 is a schematic, sectional view of the tab of FIG. 1 on a frontal side of a frame member of an orthopedic device.
Figure 4:
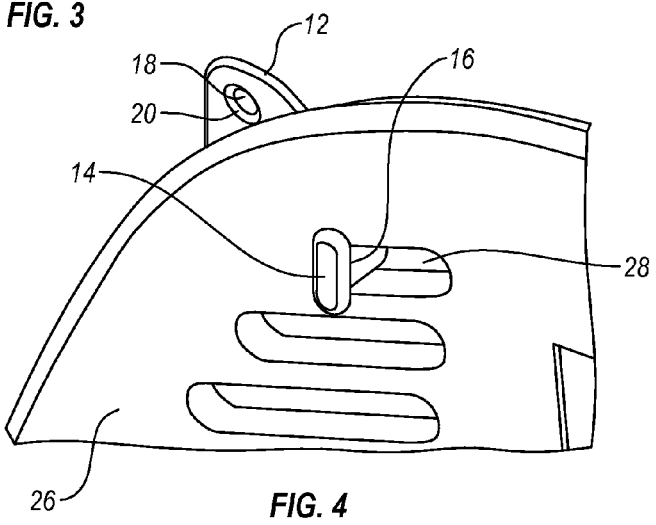
FIG. 4 is a schematic, sectional view of the tab of FIG. 1 on a rear side of a frame member of an orthopedic device.

As depicted in FIGS. 3 and 4, a frame member 26 defines a plurality of openings 28 into which the shaft 16 slides. The cross-head 14 is arranged obliquely or perpendicularly to the openings 28, permitting sliding of the tab 10 relative along a length $L_2$ of the openings to the frame member 26, and some pivoting relative to the frame member 26 without detaching from the frame member. The flanges 15, 17 are arranged flush to a surface of the frame member, and retain the tab 10 to frame member.

Referring to the embodiments of FIGS. 1-4, the cross-head 14 has a width $W_1$ less than a width $W_2$ of the openings 28 enabling the cross-head 14 to be inserted within one of the openings. In a variation, the width $W_1$ the same or greater than a width $W_2$ of the openings 28 enabling the cross-head 14 to snap into or through one of the openings 28. The ends of the flanges 15, 17 may have a taper 23 on opposed sides to facilitate snapping and insertion into the opening 28.

The cross-head 14 has a length $L_1$ is greater than the width $W_2$ of the opening 28 so the cross-head 14 is retained by the frame member 28 and slidably mounted thereto after cross-head 14 is inserted into the opening with the width $W_1$ generally parallel to the length of the opening and after being generally rotated 90 degrees so the width $W_1$ is generally perpendicular to the width $W_2$. The length $L_2$ is desirably longer than the width $W_1$ so as to allow for travel of the cross-head relative to the opening.

Figure 5:
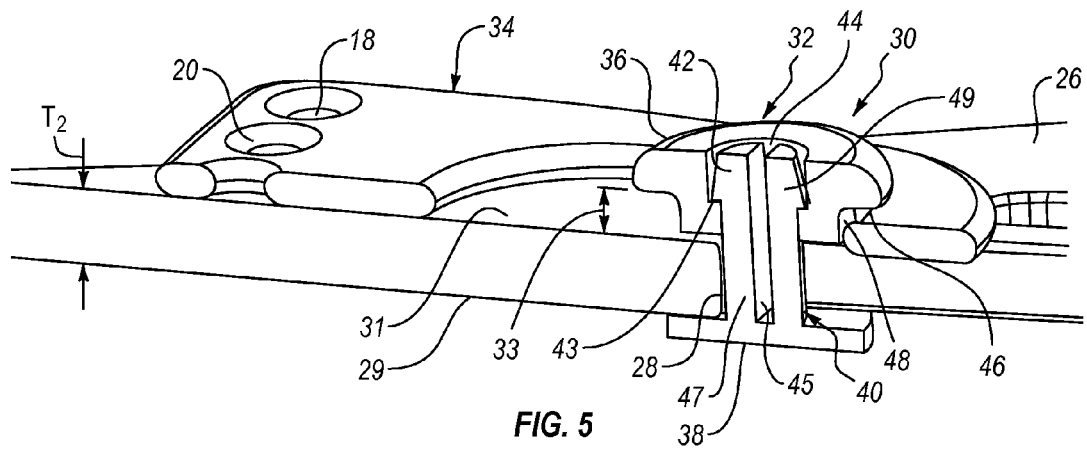
FIG. 5 is a sectional view of another embodiment of a strap attachment system on a frame member.

The shaft 16 preferably has a height $H_1$ slightly greater than a thickness $T_2$ of the frame member 26 (as depicted in FIG. 5) so at least the cross-head 14 is snugly engaging a surface of the frame member 26 to provide a tight fit but permitting slidable motion. The flanges 15, 17 have a thickness $T_1$ to sufficiently hold the tab 10 against the surface of the frame member 26 without deflection. Of course, the height $H_1$ is not limited to such a configuration and may be sized longer than the thickness of the frame member.

In a variation of the embodiment of FIGS. 1-4, the cross-section of the height 16 may be arranged so as to permit locking within the opening. For example, end portions 19 of the shaft 16 may be curved and the side walls 22 may be straight. There may be some temporary deformation of the frame member 26 about the opening 28 while inserting the cross-head 14 into the opening along its width $W_1$ parallel to the width $W_2$ of the opening 28 since a distance D between the end portions 19 may be greater than the width $W_2$. When the cross-head is rotated 90 degrees relative to the length $L_2$ of the opening after inserting the cross-head 14 through the opening 28, the side walls 22 are generally flush with the periphery of the opening 28 since the width $W_4$ between the sidewalls 22 is generally the same as the $W_2$ of the opening 28. Alternatively, the distance D may be identical to the width $W_2$.

The width $W_1$ of the cross-head 14 is less than the length $L_1$. The difference in length between the width $W_1$ and the length $L_1$ defines a length of travel of the tab 10 relative to the frame member 26 within the at least one opening 28.

The embodiment of FIGS. 1-4 allows for a strap to be secured to a frame member having a plurality of openings, and among any number of the openings. The strap can therefore be located at any number of locations, and any number of straps may be attached to the frame member to provide better security of the brace or support on the user.

The openings are configured and dimensioned to allow for the cross-head to insert therethrough when the cross-head is aligned with the openings. Once the cross-head is passed through one of the openings, the tab is rotated so the cross-head is generally perpendicular to the corresponding opening. The shape of the shaft permits the tab body to slide relative to the frame member.

The embodiments of FIGS. 5-9 describe a fastener element defining upper and lower portions. The lower portion is arranged to abut a lower surface 29 of the frame member 26, and the upper portion is arranged to substantially extend over an upper surface 31 of the frame member 26 by a clearance 33. The tab may secure between the upper portion and the second surface of the frame member within the distance defined by the clearance 33.

Figure 6:
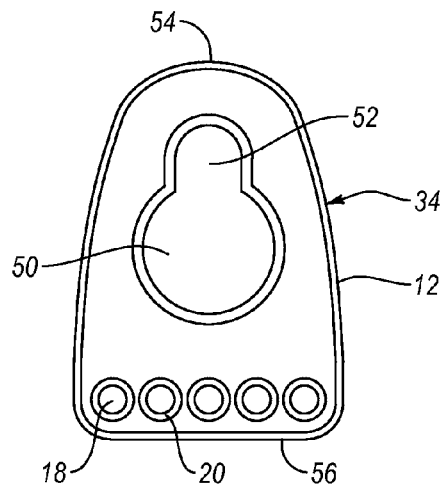
FIG. 6 is a top plan view of the tab of FIG. 5.
Figure 7:
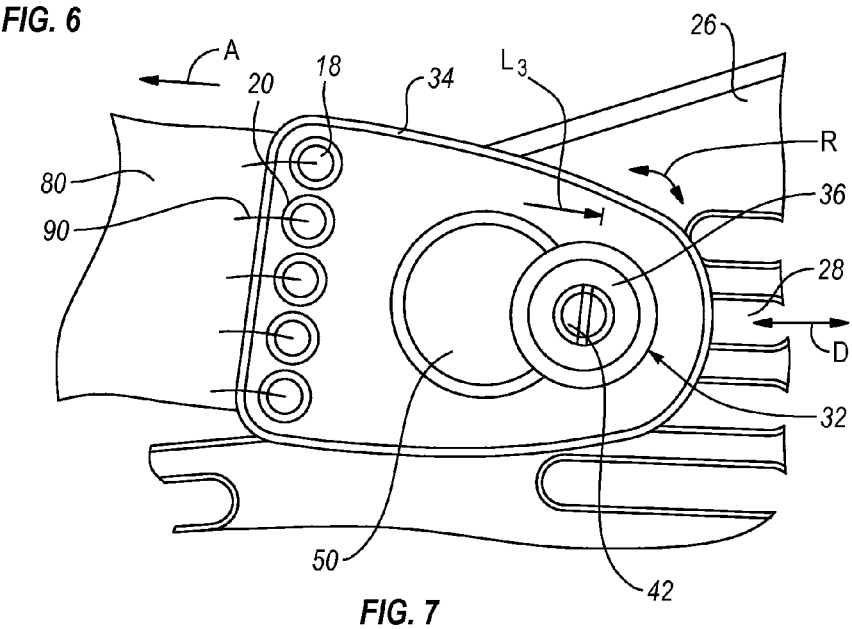
FIG. 7 is a schematic view of the strap attachment system of FIG. 5.

Turning to the strap attachment system embodiment 30 of FIGS. 5-7, a fastener element 32 in the form of a multi-body fastener element secures a keyhole tab 34 to the frame member 26. This embodiment is useful for when the frame member defines an opening 28 having a circular configuration, although it can likewise be used in an embodiment having openings, as shown in FIGS. 3 and 4.

The multi-body fastener element 32 defines a head portion 36 and a base element 38 having a snap shaft 40 extended into an opening 44 of the head portion 36. The snap shaft 40 defines a channel 45 located between opposed elongate prongs 47 dimensioned and configured to extend through the opening 28 of the frame member and the opening 44 of the head portion 36. Each of the prongs 47 has a semi-conical end 49, together forming a head 42, adapted to engage a recessed rim 43 bordering the opening 44 of the head portion 36, with the prongs 47 biased outwardly relative to the rim 43 so as form a snap fit therewith.

The head portion 36 defines an outer circular flange 46 arranged to be placed adjacent to a surface of the keyhole tab 34. The head portion 36 has a lower end portion 48 having a height generally corresponding to a thickness of the keyhole tab 34.

The keyhole tab 34 forms a main opening 50 and a slot 52 bordering and open to the main opening 50. The slot 52 has a diameter smaller than the main opening 50. The keyhole tab 34 forms a tip 54 and a widened tail section 56 along which apertures 18 having recesses 20 arranged similarly to the tab 10 of FIGS. 1 and 2.

The slot 52 generally has a diameter similar to the lower end portion 48 of the head portion 36 so the head portion 36 engages the keyhole tab 34 about the periphery of the slot 52. The main opening 50 is sized and configured to permit insertion of the head portion 36 through the main opening 50; the height of the lower end portion 48 extends to a height so the outer circular flange 46 is flush against the keyhole tab 34. It follows when head portion 36 clears the keyhole tab when inserted through the main opening, the strap 80 can be pulled a distance A corresponding to the length L between the axis of the main opening and the slot, so the multi-body fastener element retains the keyhole tab to the frame member.

FIG. 7 exemplifies how the keyhole tab can rotate R relative to the frame member, and slide a distance D relative to the frame member via the opening 28.

Figure 8:
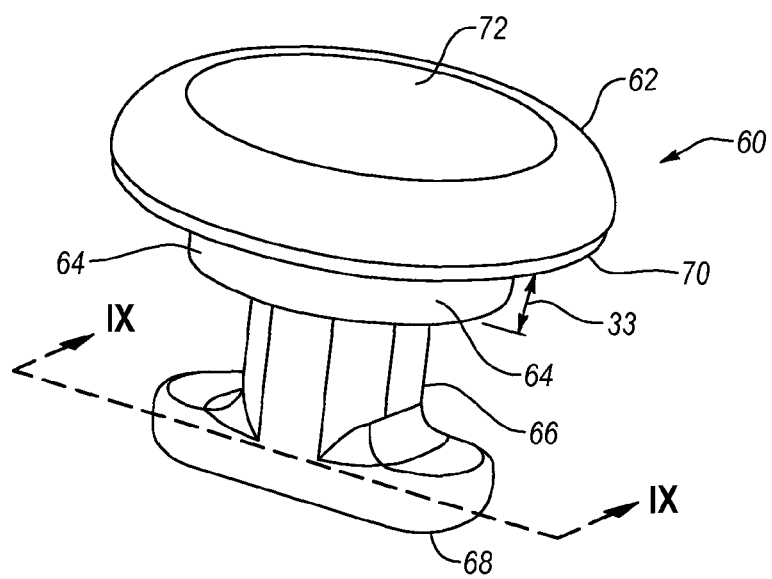
FIG. 8 is a perspective view of a single body fastener element for use in combination with the strap attachment system of FIG. 5.
Figure 9:
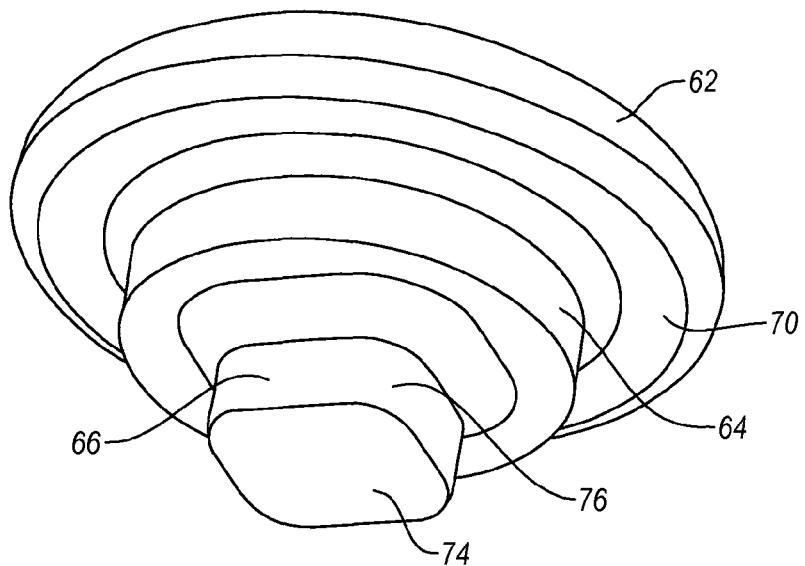
FIG. 9 is a sectional view of the single body fastener element of FIG. 8 taken along line IX-IX.

FIGS. 8 and 9 show an alternate embodiment of a single body fastener element 60. The fastener element 60 defines a head portion 62 with an overhanging flange 70 and a flat top surface 72, a circular flange 64 concentric with the head portion 62, a shaft 66 and a cross-pin 68.

The shaft 66 is not necessarily circular, and instead defines a square cross-section 74 having rounded corners 76. The rounded corners 76 provide for resistance to twisting when secured to the openings of the frame member, and once fitted to the frame member, resists further rotation so the fastener element 60 does not fall out from the opening via the cross-pin 68 aligning with the opening.

Figure 10:
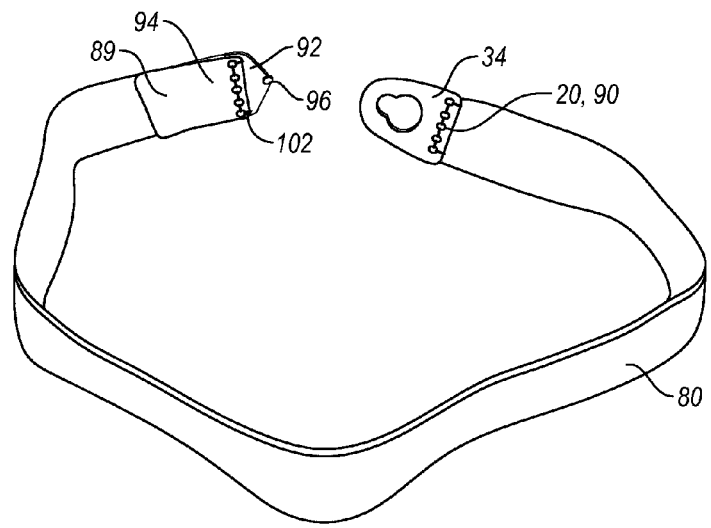
FIG. 10 is a perspective view of a strap including the tabs of FIGS. 1 and 6.
Figure 11A:
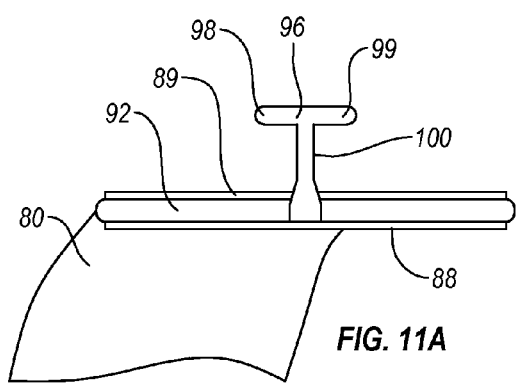
FIG. 11A is a schematic front view of the tab of FIG. 10.
Figure 11C:
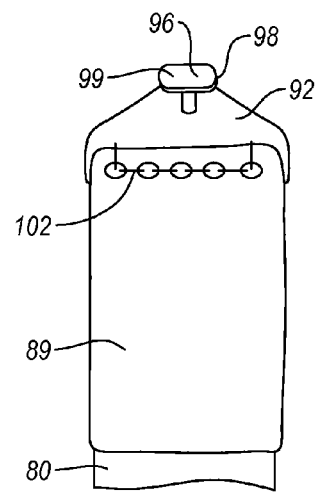
FIG. 11C is a schematic plan view of the tab of FIG. 10.
Figure 11B:
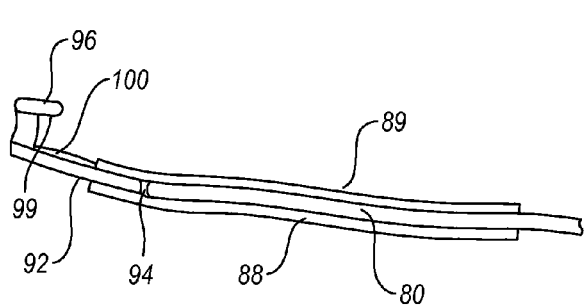
FIG. 11B is a schematic side view of the tab of FIG. 10.
Figure 11D:
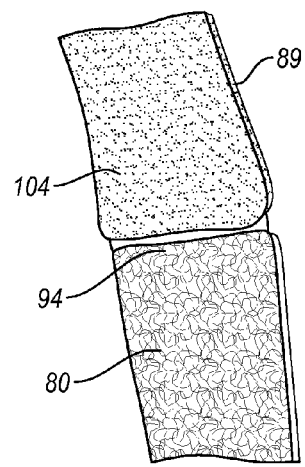
FIG. 11D is a schematic view of the tab of FIG. 11C showing removal of a strap end from the tab.

FIG. 10 exemplifies the keyhole tab 34 secured to a first end of a strap 80 and a tab 92 carrying a fastener element 96 secures to a second end 94 of a strap 80. The tab 92 is removably secured to the second end 94 of the strap 80 which may be trimmed to size according to a desired strap length.

As depicted in FIGS. 11A-11D, at least one flap 88, 89 depends from an end of the tab 92 and removably secures to the second end 94 of the strap 80. The at least one flap preferably includes a pair of flaps 88, 89 with hook elements 104 along an underside of the flaps that clamp to the second end 94 of the strap 80 and engage hook-receivable material located on or forming the strap 80. An outer surface of the flaps may preferably comprise a soft and/or hook-receivable material.

The flaps 88, 89 are removable from the strap 80 so the strap can be trimmed to an appropriate length, and the flaps 88, 89 may be stitched or otherwise secured 102 to the tab 92. The second end 94 preferably abuts an end of the tab, and the end of the tab is formed with preferably a straight edge to match a straight edge formed by second end 94 of the strap.

The fastener element 96 may be similarly formed to the fastener element of the embodiment of FIGS. 1-4, and includes flanges 98, 99 forming a cross-head and extend from an end of a shaft 100. The fastener element 96 is preferably integrally formed with a body of the tab and the shaft forms part or and protrude perpendicularly from a tip of the tab.

The keyhole tab 34 may be similarly secured to the strap and may be modified to include at least one flap that removably secures to the strap.

Figure 12:
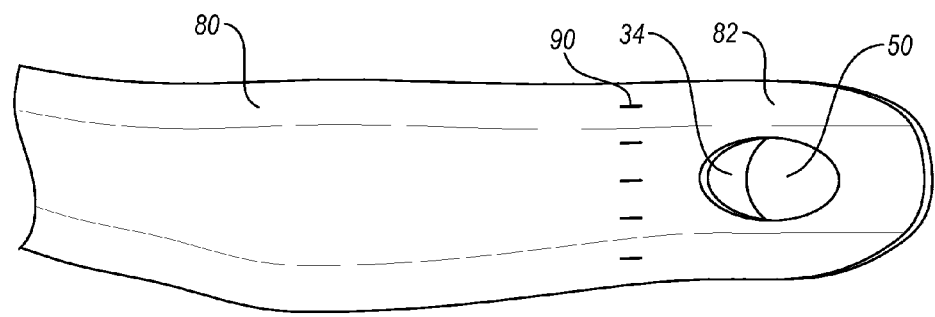
FIG. 12 is a detailed frontal view of the strap of FIG. 10 having the tab of FIG. 5.
Figure 13:
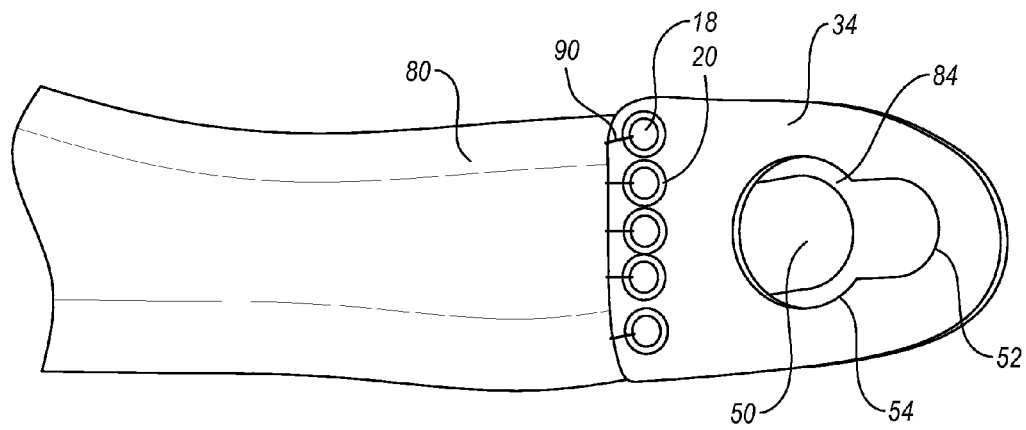
FIG. 13 is a detailed rear view of the strap of FIG. 10 having the tab of FIG. 5.

Referring to FIGS. 12 and 13, the strap 80 may have a grip extension 82 extended over a surface of the keyhole tab 34. The extension 82 has an opening 84 arranged to allow for fingers to grip the strap without grabbing the keyhole tab 34 of FIG. 6. The keyhole tab may be stitched to the strap so the keyhole tab can pivot relative to the strap, and the grip extension moves freely relative to the keyhole tab. The grip extension 82 is arranged to cover the tab so as to minimize any exposure to edges of the tab.

The dimensional relationships among the fastener element and the opening may be adopted in any of the embodiments described herein, for example the dimensions of the cross-head in the embodiment of FIGS. 1-4 can be extended to any of the embodiments described herein including the cross-head. The frame member is described generically herein and the frame member in connection with the embodiment of FIGS. 1-4 may be used with any of the embodiments described herein. An example of useable frame members is found in U.S. Pat. No. 7,198,610, granted Apr. 3, 2007 and incorporated herein by reference.

Not necessarily all such objects or advantages may be achieved under any embodiment of the invention. Those skilled in the art will recognize that the invention may be embodied or carried out to achieve or optimize one advantage or group of advantages as taught without achieving other objects or advantages as taught or suggested.

The skilled artisan will recognize the interchangeability of various components from different embodiments described herein. Besides the variations described herein, other known equivalents for each feature can be mixed and matched by one of ordinary skill in this art to construct a strap attachment system under principles of the present invention. Therefore, the embodiments described herein may be adapted to braces and supports for securing, supporting or comforting limbs or other anatomy.

Although this invention has been disclosed in certain preferred embodiments and examples, it will be understood by those skilled in the art that the present invention extends beyond the disclosed embodiments to other alternative embodiments and/or uses of the invention and obvious modifications and equivalents thereof. It is intended that the scope of the present invention herein disclosed should not be limited by the disclosed embodiments described above, but should be determined only by a fair reading of the claims that follow.

The invention claimed is:

1. A strap attachment system, comprising:
    a frame member having an opening;
    a strap;
    a tab connecting to the strap, and defining a body and a fastener element extending from the body and arranged to be engaged to the frame member via the opening, the tab being slidably movable relative to the frame member within the opening, the strap connecting to the tab;
    wherein at least one flap flexibly depends from an end of the tab, and removably securing to the strap.

2. The strap attachment system of claim 1, wherein the fastener element includes a shaft and a cross-head carried, the shaft having a height at the least the same as a thickness of the frame member.

3. The strap attachment system of claim 2, wherein the cross-head defines a first width substantially the same as a second width defined by the opening.

4. The strap attachment system of claim 2, wherein the cross-head has a first length greater than a second width defined by the opening.

5. The strap attachment system of claim 2, wherein the cross-head has a first width less than a second length defined by the opening, the difference in length between the first width and the second length defining a length of travel of the tab relative to the frame member within the opening.

6. The strap attachment system of claim 2, wherein the shaft defines first and second side walls opposed from one another and spaced apart by a third width, the third width is substantially the same as a second width of the opening, the first and second side walls arranged perpendicular to a first length of the cross-head.

7. The strap attachment system of claim 6, wherein the shaft defines first and second end portions opposed from one another and generally perpendicular to the side first and second side walls.

8. The strap attachment system of claim 7, wherein a distance between the first and second end portions is greater than a second width defined by the opening, the shaft insertable through the opening wherein the first and second side walls are arranged perpendicular to the second width, and the at least one frame member is resilient as the shaft is pressed through the opening, the shaft is arranged for rotation within the opening so as to arrange the first and second side walls parallel to the second width.

9. The strap attachment system of claim 1, wherein the body defines a second end flaring outwardly from the first end of the body, and the cross-head extends generally parallel to the second end of the body.

10. A method for attaching a strap connected to a tab to a frame member having an opening, the method comprising the steps of:
    arranging a fastener element having a shaft carrying a cross-head in the opening by orienting a width of the cross-head parallel to a length of the opening, the fastener element connecting the strap to the frame member by the tab;
    inserting the cross-head through the opening so as extend over a surface of the frame member;
    turning the fastener element so the width of the cross-head is perpendicular to the length of the opening with the shaft extending through the opening;
    wherein the shaft has portions defining a dimension resisting turning within the opening such that upon overcoming resistance within the opening, the shaft has a dimension generally the same as a width of the opening.

11. A strap attachment system, comprising:
    a frame member having an opening;
    a strap;
    a tab connecting to the strap, and defining a body and a fastener element extending from the body and arranged to be engaged to the frame member via the opening, the tab being slidably movable relative to the frame member within the opening, the strap connecting to the tab;
    wherein the fastener element includes a shaft and a cross-head carried, the shaft having a height at the least the same as a thickness of the frame member;
    wherein the shaft defines first and second side walls opposed from one another and spaced apart by a third width, the third width is substantially the same as a second width of the opening, the first and second side walls arranged perpendicular to a first length of the cross-head.

* * * * *